United States Patent
Murray

(10) Patent No.: US 9,795,308 B2
(45) Date of Patent: Oct. 24, 2017

(54) DEVICE FOR MEASURING BRACHIAL BLOOD PRESSURE IN AN INDIVIDUAL

(71) Applicant: BP ALERT LIMITED, Galway, County Galway (IE)

(72) Inventor: Dermot Jerome Murray, Galway (IE)

(*) Notice: Subject to any disclaimer, the term of this patent is extended or adjusted under 35 U.S.C. 154(b) by 0 days.

(21) Appl. No.: 14/430,732

(22) PCT Filed: Sep. 24, 2013

(86) PCT No.: PCT/EP2013/069864
§ 371 (c)(1),
(2) Date: Mar. 24, 2015

(87) PCT Pub. No.: WO2014/048924
PCT Pub. Date: Apr. 3, 2014

(65) Prior Publication Data
US 2015/0250390 A1 Sep. 10, 2015

(30) Foreign Application Priority Data
Sep. 28, 2012 (WO) ............... PCT/EP2012/069167

(51) Int. Cl.
*A61B 5/02* (2006.01)
*A61B 5/022* (2006.01)
(Continued)

(52) U.S. Cl.
CPC ............. *A61B 5/022* (2013.01); *A61B 5/024* (2013.01); *A61B 5/02116* (2013.01);
(Continued)

(58) Field of Classification Search
CPC ... A61B 5/021; A61B 5/0205; A61B 5/02028; A61B 5/024; A61B 5/0402;
(Continued)

(56) References Cited

U.S. PATENT DOCUMENTS 5,368,039 A    11/1994  Moses
5,879,307 A     3/1999  Shiu-Shin
(Continued)

FOREIGN PATENT DOCUMENTS

EP    1568314 A1    8/2005
WO   2011061732 A2  5/2011

OTHER PUBLICATIONS

International Search Report / PCT/EP2013/069864 / dated Feb. 13, 2014 / Date of Completion Feb. 5, 2014.

*Primary Examiner* — Deborah Malamud
(74) *Attorney, Agent, or Firm* — Fulwider Patton LLP

(57) ABSTRACT

A device for measuring brachial arterial blood pressure in an individual has a blood pressure cuff attachable to an upper arm, means, separate to the blood pressure cuff, for measuring the heart rate, and a control unit connected to both the blood pressure cuff and the heart rate monitoring means, such that, in use, the control unit monitors the heart rate for the establishment of a stable resting heart rate, initiates a blood pressure measurement, and calculates the pulse pressure (PP) to establish the status of the brachial artery during the blood pressure measurement. Where the heart rate drops to within +12 bpm of a reference, resting heart rate for the individual the device will initiate a blood pressure measurement in accordance with a reference, resting heart rate protocol. However, where an irregular heart rate (IRHR) is found the device will initiate a blood pressure measurement in accordance with a timed protocol.

10 Claims, 8 Drawing Sheets

(51) Int. Cl.
*A61B 5/00* (2006.01)
*A61B 5/024* (2006.01)
*A61B 5/021* (2006.01)

(52) U.S. Cl.
CPC ...... *A61B 5/02416* (2013.01); *A61B 5/02438* (2013.01); *A61B 5/6826* (2013.01); *A61B 5/6838* (2013.01); *A61B 5/7282* (2013.01)

(58) Field of Classification Search
CPC ....... A61B 5/7264; A61B 5/6802; A61B 5/02; A61B 5/0245; A61B 7/04; A61B 2562/0247; A61B 5/7221; A61B 2562/164; A61B 5/00; A61B 5/0004; A61B 5/04; A61B 5/683; A61B 5/02427; A61B 5/0468; A61B 5/6804; A61B 5/6824; A61B 5/6831; A61B 7/00; A61B 7/02; A61B 8/04; A61N 1/36117; A61N 1/36564; A61N 1/08; A61N 1/36139; A61N 1/3702; A61N 1/3937; A61M 2205/3344; A61M 2230/04; A61M 2230/30; A61M 5/1723; G06F 19/345; G08B 21/0453
See application file for complete search history.

(56) References Cited

U.S. PATENT DOCUMENTS

| | | |
|---|---|---|
| 6,050,951 A | 8/2000 | Friedman |
| 7,211,047 B2 | 5/2007 | Chan |
| 7,976,471 B2* | 7/2011 | Martin ................ A61B 5/0048 600/485 |
| 2011/0009718 A1 | 1/2011 | Gavish |
| 2011/0160598 A1 | 6/2011 | Yamashita |
| 2011/0230729 A1 | 9/2011 | Shirasaki et al. |
| 2011/0234597 A1 | 9/2011 | Kohut |

\* cited by examiner

DEVICE FOR MEASURING BRACHIAL BLOOD PRESSURE IN AN INDIVIDUAL

CROSS-REFERENCE TO RELATED APPLICATIONS

This application is based upon and claims the benefit of priority from the prior Patent Application No. PCT/EP2013/069864, filed on Sep. 24, 2013, which claims priority from PCT/EP2012/069167 filed Sep. 28, 2012, the entire contents of which are incorporated herein by reference.

TECHNICAL FIELD

This invention relates to a device for measuring brachial blood pressure in an individual, and, in particular, to a device for monitoring brachial blood pressure outside of a clinical setting.

BACKGROUND ART

Hypertension is a continuous, independent, yet modifiable risk factor for cardiovascular, cerebrovascular and renal disease. It has been estimated that 62% of cerebrovascular disease and 49% of ischemic heart disease can be attributed to sub-optimal blood pressure control. For this reason one of the most commonly performed test in a doctor's surgery is blood pressure measurement.

The measurement of brachial blood pressure using an inflatable cuff, results in a systolic blood pressure reading and a diastolic blood pressure reading. The readings are typically in millimeters of mercury mmHg (a mmHg being equivalent to 133.3223684211 pascals (Pa)). A number of factors can affect the accuracy of these blood pressure readings, and the following table lists some of these (Handler, Joel, The Permanente Journal/Summer 2009/Volume 13 No. 3, pages 51-54).

| Factors affecting accuracy of blood pressure measurements | |
|---|---|
| Factor | Magnitude of systolic/diastolic blood pressure discrepancy (mmHG) |
| Talking or active listening | 10/10 |
| Distended bladder | 15/10 |
| Cuff over clothing | 5-50/ |
| Cuff too small | 10/2-8 |
| Smoking within 30 minutes of measurement | 6-20/ |
| Paralyzed arm | 2-5/ |
| Back unsupported | 6-10/ |
| Arm unsupported, sitting | 1-7/5-11 |
| Arm unsupported, standing | 6-8/ |

Even when the above factors are taken into account, another factor, which can affect the accuracy of the reading is the "white coat effect" (WCE). Thus, the blood pressure in certain individuals will rise when a doctor takes the blood pressure reading, particularly in the doctor's surgery.

Automated blood pressure devices are known, which are designed to negate any WCE errors for an individual. Thus, the bpm-100, manufactured by BPTru Ltd, of Unit 1, 1850 Hartlet Avenue, Coquitlam, BC, Canada V3K 7A1, is an automated blood pressure monitor, which, without an operator's assistance, takes six blood pressure readings, discards the first one and automatically computes the average of the remaining five readings.

However, a problem with this approach is that, even though a doctor/operator is not involved, the individual's blood pressure readings may still be elevated, as he has not reached a relaxed state before the taking of the readings commences.

In most cases, this inaccuracy is caused by two contributing factors: a failure to allow the cardiovascular and nervous systems to reach a completely stable parasympathetic state and an inability to identify when this state has been reached.

When the body is at rest the human heart rate drops causing a corresponding drop in blood pressure (BP) across the peripheral vascular system. In order to maintain adequate delivery of blood to peripheral tissues the system must compensate for the drop in BP by increasing blood flow. It does this by dilating the vessels. As the heart rate lowers, the sympathetic nervous system controlling vasoconstriction is turned off and the parasympathetic nervous system is activated, causing vasodilation. It can, in some cases, take time for the cardiovascular system to reach this completely stable parasympathetic state due to environmental or physiological conditions. Failure to wait for this completely stable parasympathetic state to be reached will result in an inaccurate BP reading and could lead to the misdiagnosis of a patient's blood pressure status; this applies both to hypertension and hypotension.

Thus, there is a need for a device for measuring brachial blood pressure in an individual which provides accurate blood pressure readings and avoids the aforementioned situations leading to inaccurate readings.

Furthermore, there is a need for a device, which will give accurate results outside the clinical setting, when used, for example as a home blood pressure monitor.

DISCLOSURE OF INVENTION

Thus, the invention provides a device for measuring brachial arterial blood pressure in an individual, the device comprising a blood pressure cuff attachable to an upper arm of the individual, means, separate to the blood pressure cuff, for measuring the heart rate of the individual, and a control unit connected to both the blood pressure cuff and the heart rate measuring means, such that, in use, the control unit monitors the heart rate of the individual for the establishment of a stable, resting heart rate, initiates a blood pressure measurement using a protocol appropriate to the outcome of the heart rate monitoring, and calculates the pulse pressure (PP) to establish the status of the brachial artery during the blood pressure measurement.

By blood pressure cuff in this context is meant an inflatable brachial blood pressure cuff, pump unit and associated electronics.

The pulse pressure (PP) is defined as the difference between the systolic blood pressure (SBP) and the diastolic blood pressure (DBP).

An advantage of the device according to the invention is that it automatically waits until the individual is in a resting state and his cardiovascular system is in a stable parasympathetic state, before initiating the blood pressure measurement. This removes the danger of inaccurate blood pressure readings being recorded, due to the individual not waiting for a sufficient length of time to reach a resting state. Thus, the device is not only seeking a stable resting heart rate before initiating a blood pressure measurement but is also seeking to confirm dilation of the brachial artery by monitoring the calculated PP.

A further advantage of the device according to the invention is that the heart rate measuring means is separate from the blood pressure cuff. Thus, operation of the blood pressure cuff will have a negligible effect on the heart rate readings.

The separate heart rate measuring means provides a real-time heart rate. Whereas, a brachial blood pressure cuff, incorporating a heart rate monitor, cannot provide a real-time heart rate output while the cuff is operating, and cannot provide any heart rate output between tests.

Preferably, the heart rate measuring means is a finger clip heart rate monitor.

Finger clip heart rate monitors provide accurate heart rate readings.

Further, preferably, the finger clip heart rate monitor is attachable, in use, to a finger on the hand of one arm of the individual and the blood pressure cuff is attachable to the other arm.

An advantage of this arrangement is that the operation of the blood pressure cuff will not affect the heart rate measured on the finger of the other arm.

In one embodiment of the device according to the invention the control unit will initiate a blood pressure measurement using a resting heart rate protocol, once the measured heart rate has dropped to within +15 bpm of a reference, resting heart rate for the individual, which reference, resting heart rate has been previously established for the individual during initial assessment by monitoring the heart rate for a period of 1000 to 1400 s and identifying the minimum heart rate for the period, which minimum heart rate is defined as the reference, resting heart rate for the individual.

The condition of the patient's vascular tone is not measured directly. The vascular tone is instead inferred through observation of the patient's heart rate. When the heart rate has reached a steady, resting level, vascular tone is deemed to be in its most relaxed and fully dilated state. When measuring heart rate for the first time, extra care is taken to ensure the vasculature has reached a fully parasympathetic state. The results from this first test are used as a reference point for future tests.

Because the device according to the invention will not take a blood pressure reading until it has inferred that a completely stable parasympathetic state has been reached, results obtained from the device are more consistent, accurate and repeatable than for prior art devices. This advantage is of particular importance in taking accurate BP readings in a non-clinical setting.

Preferably, the control unit establishes that the heart rate remains at or below +12 bpm of the reference, resting heart rate for a period within the range of 100 to 140 s, before a blood pressure measurement is initiated.

The closer the heart rate equates to the reference, resting heart rate the more repeatable will be the blood pressure results.

Further, preferably, the control unit records a plurality of blood pressure readings, while continuing to monitor the heart rate to ensure that it remains at or below +12 bpm of the reference, resting heart rate during each blood pressure reading, calculates the corresponding mean arterial pressure (MAP) and PP for each blood pressure reading, and stores each MAP reading, together with the corresponding PP, heart rate, systolic pressure reading and diastolic pressure reading, as a set of data.

The MAP is a term used in medicine to describe an average aortic blood pressure in an individual. It is defined as the average arterial pressure during a single cardiac cycle.

At normal resting heart rates MAP can be approximated using the more easily measured SBP and DBP, using the following approximation:

$$MAP \approx ((2 \times DBP) + SBP)/3$$

An advantage of taking a plurality of blood pressure readings is that the best results for a particular group of blood pressure readings will be used to monitor the individual.

In a further embodiment of the device according to the invention the control unit will initiate a blood pressure measurement using a timed protocol, where the measured heart rate does not stabilize to within +15 bpm of the reference, resting heart rate.

In certain situations, such as where an individual has recently imbibed a beverage containing alcohol or caffeine, and for a variety of other reasons, an individual's heart rate will not fall to within +15 bpm of the reference, resting heart rate. However, rather than not testing the individual's blood pressure at all, the control unit will initiate the measurement using the timed rate protocol.

Preferably, the control unit will initiate a blood pressure measurement using a timed protocol, where the measured heart rate does not remain at or below +12 bpm of the reference, resting heart rate for a period within the range of 100 to 140 s, due to the presence of arrhythmia.

Thus, even though an individual's heart rate might be below +12 bpm, if this heart rate level is not maintained over a period of 100 to 140 s then a test based on the timed protocol will be initiated.

Preferably, the control unit records a plurality of blood pressure readings at timed intervals, calculates the corresponding MAP and PP for each set of readings, and stores each MAP reading, together with the corresponding PP, heart rate, systolic pressure reading and diastolic pressure reading, as a set of data.

When the control unit is operating under the timed rate protocol the blood pressure is measured despite the reference, resting heart rate not being achieved. The measurements are made at timed intervals and a change in heart rate will not cause a measurement to be aborted. While the results achieved will be less accurate it is better to have some results than none at all.

Suitably, four sets of data are recorded.

Four sets of data have been found to be sufficient to provide accurate readings.

In a further embodiment of the device according to the invention the control unit analyses the four sets of data and classifies the blood pressure into one of six WHO (World Health Organisation) classifications using the systolic or diastolic pressure value, whichever value results in the higher classification.

The WHO categorises a patient's blood pressure based on systolic and diastolic pressure ranges. Blood pressure is displayed using the WHO Indicator. Where the four set of data have been derived using the resting heart rate protocol the systolic or diastolic pressure value is used to set the WHO Indicator on the report. This gives the most accurate classification of the individual's blood pressure.

In a further embodiment of the device according to the invention the control unit analyses the four sets of data and classifies the blood pressure into one of six WHO classifications using the derived MAP value.

When the four sets of data have been derived using the timed protocol the device uses the calculated MAP result rather than the separate systolic or diastolic readings to categorise the individual's blood pressure. This provides the best indication of the WHO classification into which the patient's blood pressure falls. Where arrhythmia is present the separate systolic or diastolic readings would not be consistent, whereas the derived MAP values for each set of data would be more consistent.

Preferably, the control unit prepares a report indicating the validity of the test, the values for heart rate, systolic blood pressure, diastolic blood pressure, MAP, PP and the WHO classification into which the individual falls.

Presenting the results in this fashion, each time the individual's blood pressure is monitored, simplifies the interpretation of a particular result and the comparison of recent results to identify any trend in the results over time.

Further, preferably, the report will be flagged for repeat if the PP is greater than 55 mmHg, except in the case where arrhythmia has been found.

An advantage of this feature is that, where an individual cannot reach a fully rested state before the blood pressure measurement is initiated, nevertheless the device will run the tests in accordance with the appropriate protocol, so that a blood pressure reading is available for monitoring purposes. The resulting report will indicate that the PP has not dropped below 60 mgHg, indicating that the brachial artery has not dilated.

In a further embodiment of the device according to the invention the control unit has means for transmitting the and each set of data to a remote data centre.

An advantage of connection to a remote data centre is that data for a large number of individuals can be stored on the database and the data for each individual can be accessed and analysed without having to access the results on each local blood pressure device.

Preferably, the remote data centre analyses the and each set of data, derived using the resting heart rate protocol, and classifies the blood pressure into one of six WHO classifications using the systolic or diastolic pressure value, whichever value results in the higher classification.

In a further embodiment of the device according to the invention, the remote data centre analyses the and each set of data, derived using the timed test protocol, and classifies the blood pressure into one of six WHO classifications using the derived MAP value.

Preferably, the control unit has means for receiving a report, from the remote data centre, for review by the individual.

Thus, the data centre can draw up a report for the individual and send it back to the particular blood pressure device.

In a further embodiment of the device according to the invention, when the report warrants further action by the individual or by the individual's clinician, the remote data centre alerts a monitoring station, which contacts the appropriate person.

The advantage of the addition of a monitoring station is that assistance can be organised for an individual where the results indicate that it is needed. Personnel at the monitoring station will follow up on any adverse results and ensure that the appropriate person is contacted.

A further advantage of this arrangement is that large numbers of individuals in separate locations can be monitored and managed by the one monitoring station with a resultant economy of scale.

In a further embodiment of the device according to the invention, the data centre can remotely reset the test parameters for the device based on the sets of data received.

Thus, for example, where it appears that an individual's reference, resting heart rate has changed, this new value can be programmed into the individual's device from the data centre.

In a further embodiment of the device according to the invention, where the individual's age is within the range of 10 to 50 years and one of the recorded MAP readings is less than 100+/−5, the control unit compares the percentage difference of the four MAPs recorded and where the percentage difference is greater than 13 to 17% then, where one of the PP readings is greater than 55+/−5, the control unit compares the percentage difference of the four recorded PPs, and where the percentage difference is greater than 18 to 22%, the report will include an indication of a possible presence of aortic valve regurgitation.

In a further embodiment of the device according to the invention, where the individual's age is within the range of 15 to 40 years and one of the recorded MAP readings is less than 100, the control unit compares the percentage difference of the four MAPs recorded and where the percentage difference is greater than 15% then, where one of the PP readings is greater than 55, the control unit compares the percentage difference of the four recorded PPs, and where the percentage difference is greater than 20%, the report will include an indication of the possible presence of aortic valve regurgitation.

Aortic valve regurgitation, also referred to as aortic regurgitation, is a condition that occurs when the aortic valve does not close tightly, thus allowing some of the blood, which has been pumped from the left ventricle, to leak back.

Most often, aortic valve regurgitation develops gradually, and a flexible aorta compensates for the problem. The person may have no signs or symptoms for many years, and may be unaware that they have the condition. However, as an individual ages, the aorta becomes stiffer and can no longer compensate.

Thus, an advantage of the device in accordance with the invention is that the presence of aortic valve regurgitation can be detected by analysis of a set of blood pressure results, even in an individual who is not exhibiting any symptoms of the condition.

Where the possible presence of aortic regurgitation is indicated by the device, the device will initiate of number of further blood pressure measurements so as to verify the indication of aortic valve regurgitation.

It will be understood that further tests and medical examination of the individual will be required to confirm the presence of aortic valve regurgitation.

In a further embodiment of the invention, a drop in the diastolic blood pressure of between 8 to 15% from the value recorded during a previous testing session triggers the device to check for the possible presence of aortic valve regurgitation.

An advantage of the device in accordance with the invention is that it will automatically check the data, for a particular patient, for the possibility of aortic regurgitation, when a drop in the patient's diastolic pressure is detected. One reason for a drop in the diastolic pressure could be the leaking of blood back through the aortic valve and this may be confirmed when the MAP and PP values are checked.

In a further embodiment of the invention, the control unit checks the PP readings before, if necessary, checking the MAP readings.

It will be readily appreciated that the sequence of checking the MAP and PP readings may be reversed.

In a further embodiment of the device according to the invention, the operation of the device is remotely controllable via an Internet connection.

An advantage of having the capability of remotely controlling the device is that it addresses any uncertainty or doubt held by the individual as to the device's correct operation.

A further advantage is that the device can be remotely operated in the situation where the individual is unable to operate the device unaided.

BRIEF DESCRIPTION OF DRAWINGS

The invention will be further illustrated by the following description of an embodiment thereof, given by way of example only with reference to the accompanying drawings in which.

MODE OF CARRYING OUT THE INVENTION

Figure 1:
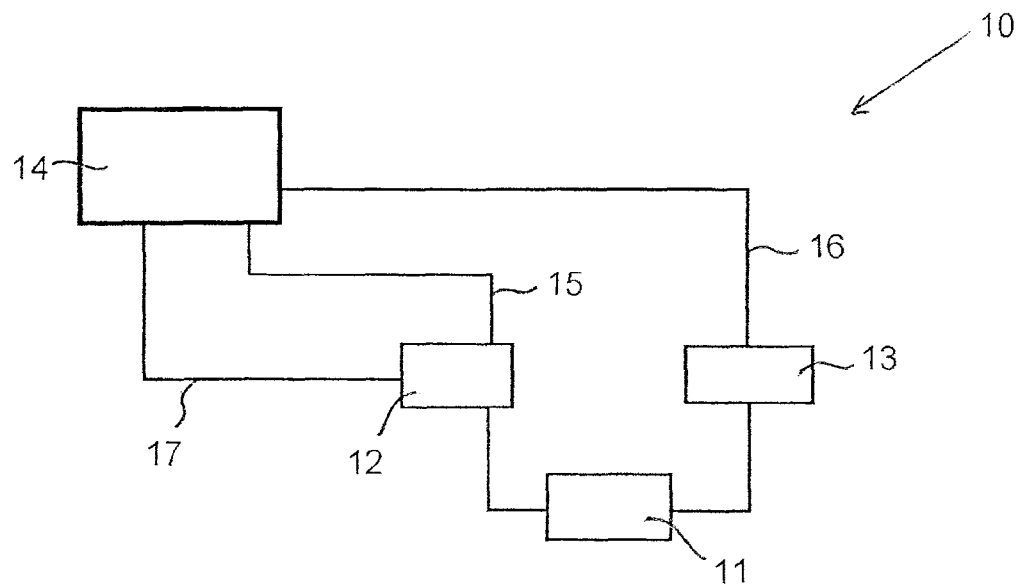
FIG. 1 is a schematic representation of a blood pressure device in accordance with the invention.

Referring to FIG. 1, there is illustrated generally at 10, a device for measuring brachial blood pressure in an individual 11, which device 10 comprises a blood pressure cuff 12, which is attachable to one arm of the individual 11 and means 13, separate to the blood pressure cuff 12, for measuring the heart rate of the individual 11, which is attachable to the other arm of the individual 11.

A control unit 14 is connected to both the blood pressure cuff 12 and the heart rate measuring means 13, such that, in use, the control unit 14 monitors the heart rate of the individual 11 for a stable, resting heart rate and initiates a blood pressure measurement using a protocol appropriate to the results of the heart rate monitoring.

The blood pressure cuff 12 is a UA-767PC automated blood pressure monitor, manufactured by A&D Medical, of 1756 Automation Parkway, San Jose, Calif. 95131, USA.

The heart rate measuring means 13 is a Nonin Xpod 3012LP oximeter with an 8000AX series finger clip, both manufactured by Nonin Medical Inc, based in Minneapolis, USA, which will be hereinafter referred to as a finger clip unit 13.

The control unit 14 is a personal computer.

The blood pressure cuff 12 and the finger clip unit 13 are directly connected to the control unit 14 by wires 15 and 16 respectively. The operation of the blood pressure cuff 12 is controlled from the control unit 14, through a wire 17.

The control unit 14 receives the blood pressure readings from the blood pressure cuff 12, together with the heart rate readings from the finger clip unit 13, processes the results and generates a report, either on screen (not shown) or as a print-out.

Figure 2:
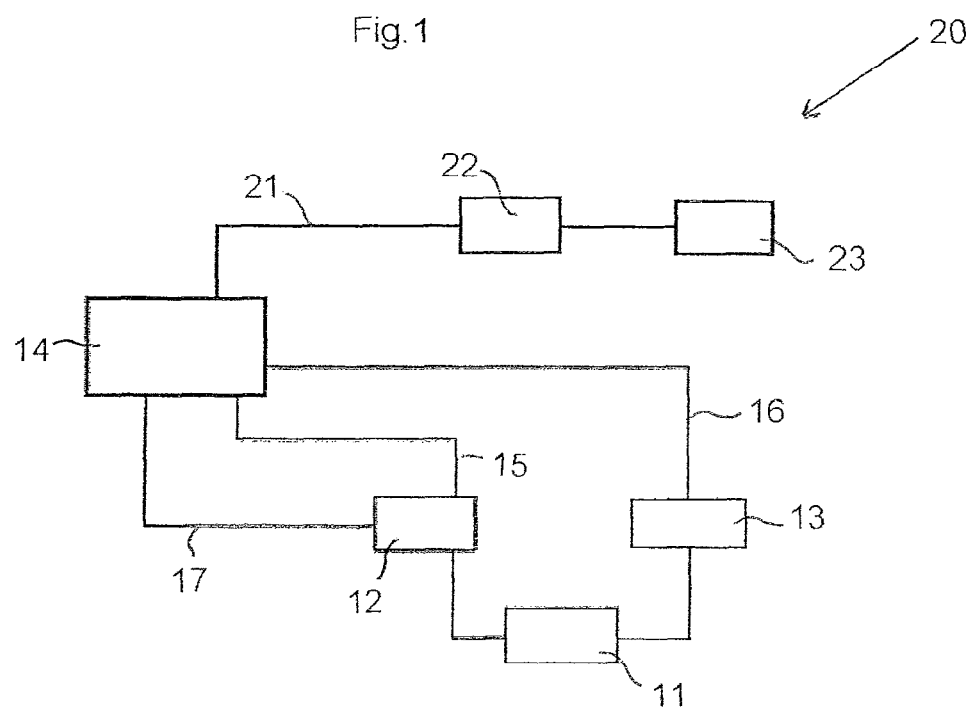
FIG. 2 is a schematic representation of an alternative embodiment of a blood pressure device in accordance with the invention.

Referring to FIG. 2, an alternative embodiment of a device for measuring brachial blood pressure is illustrated generally at 20, and like features are given the same reference numerals.

In the device 20 the control unit 14 receives the blood pressure readings from the blood pressure cuff 12, together with the heart rate readings from the finger clip unit 13 and transmits them through a wireless connection 21 to a data centre 22, where the results are processed and a report generated. If the report warrants further action by the individual or the individual's clinician, then the data centre 22 alerts a monitoring station 23, which contacts the appropriate person.

Before using either device 10; 20, a pre-operational protocol and checklist has to be followed. The pre-operational protocol ensures that factors that can influence the accuracy and reliability of the test, including mental stress and biological stimulants, are kept to a minimum. Below is a list of some of the common causes of artificially elevated blood pressure results that the pre-operational protocol addresses.

No Rest Taken Before Test: It is necessary to rest in a quiet and comfortable environment for 3-5 minutes prior to taking your blood pressure. It can take up to a further 12 minutes for the cardiovascular system to reach a state in which an accurate blood pressure measurement can be taken. Activities such as exercise or eating can affect your systolic pressure by 10-20 mmHg so resting before testing is important.

Cuff Worn Over Clothing: The BP Cuff should be worn directly on the arm, not over any clothing. Applying the BP cuff over clothing can increase your systolic pressure by between 10-50 mmHg.

Cuff Too Small: Ensuring that the correct cuff is being worn for a test is extremely important. Wearing the wrong cuff can affect your systolic pressure by between 10-40 mmHg. A specific cuff is available that is designed for use on children aged younger than 15 years.

Full Bladder: Taking a blood pressure test on a full bladder has been shown to produce higher results, with systolic pressures of 10-15 mmHg higher than normal.

Cold Temperature: Your blood pressure tends to increase when you are cold. Your systolic pressure can rise by as much as 30 mmHg and your diastolic by as much as 20 mmHg when you take your blood pressure in cold conditions.

Smoking: Any products that contain nicotine, including cigarette substitutes such as gum or inhalers, will raise your systolic pressure by 5-10 mmHg. You should refrain from smoking before you take your test.

Alcohol/Caffeine: Alcohol and caffeine, like nicotine, cause your systolic pressure to temporarily rise by 5-10 mmHg. Additionally, these substances also increase your heart rate. It is important to keep your heart rate at a low and steady level before a successful blood pressure test can be performed.

Talking: Talking whilst having your blood pressure taken can raise your systolic blood pressure by 10-15 mmHg.

Negative Emotional State: Emotions such as stress or anxiety can have a big impact on your state of mind as well as your blood pressure. Being tense, distracted or worried during your test can raise your systolic blood pressure by 10-15 mmHg and your diastolic by 4-8 mmHg. It is best practice to be calm and relaxed when you take your test. Ensure your mind is not focused on anything in particular, you are taking in a broad visual view and you are not distracted or thinking about anything stressful or detailed (e.g. phone calls you have to make, your list of errands).

Uncomfortable/Incorrect Testing Position: You should be seated in a comfortable position with support on your back, your legs uncrossed and your feet planted on the floor. The cuff should be at the level of your heart with good support for your arm to rest on. Being in an uncomfortable or incorrect position for your blood pressure test can result in an increase in your systolic pressure of up to 8 mmHg.

The operation of the device in accordance with the invention will be described with reference to the device 20, as illustrated in FIG. 2.

Initial Screening Test to Establish a Resting Heart Rate

Where the individual 11 is being tested for the first time an initial screening test protocol is followed. This initial screening test protocol includes an account setup procedure followed by the evaluation of the individual's resting heart rate.

The individual 11 adopts a resting position and the finger clip unit 13 is attached to a finger.

Figure 3:
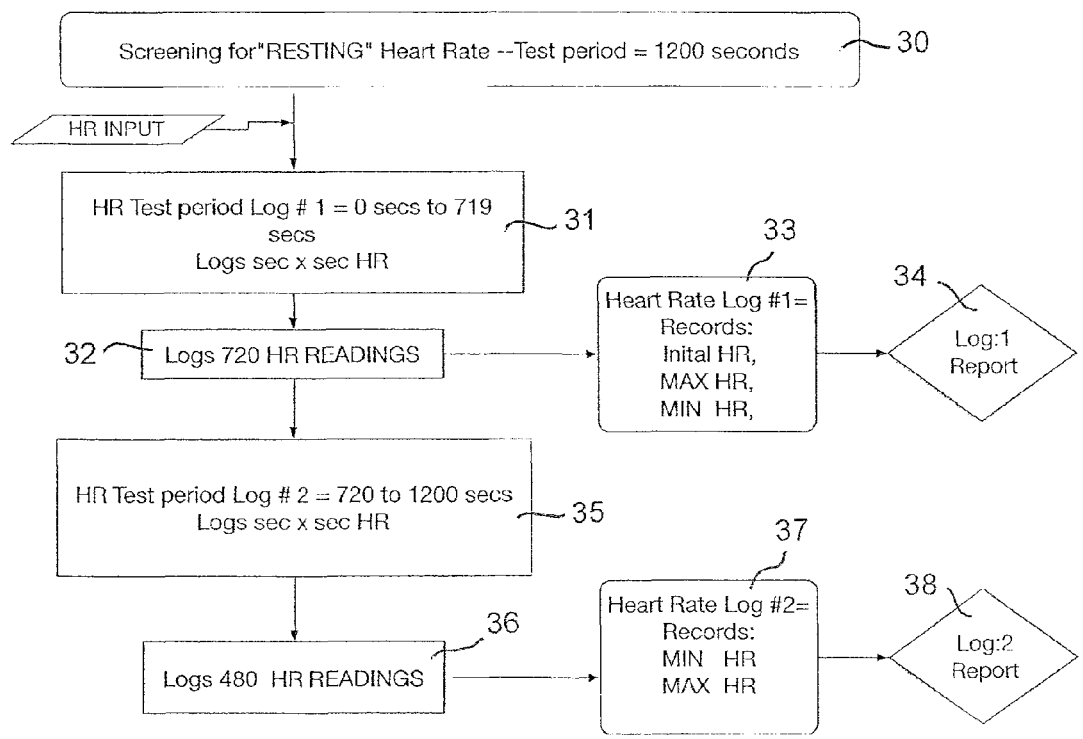
FIG. 3 is the first page of a flowchart of an initial heart screen for the blood pressure device in accordance with the invention.

Referring to FIG. 3, which is a flowchart of the screening test protocol, the screening test is 1200 seconds (s) in duration 30 and is split into two separate sections, Log 1 and Log 2, with no break in between.

Log 1 runs from 0 to 719 s and the heart rate (HR) is logged second by second 31. This results in a total of 720 heart rate recordings 32.

The initial heart rate, the maximum heart rate, and the minimum heart rate values are extracted from the 720 heart rate recordings 33 and these three parameters, together with the 720 heart rate recordings, together form the contents of the Log 1 report 34.

Log 2 runs from 720 to 1200 s and again the heart rate is logged second by second 35. This results in a total of 480 heart rate recordings 36.

The maximum heart rate, and the minimum heart rate values are extracted from the 480 heart rate recordings 37 and these two parameters, together with the 480 heart rate recordings, together form the contents of the Log 2 report 38.

Figure 4:
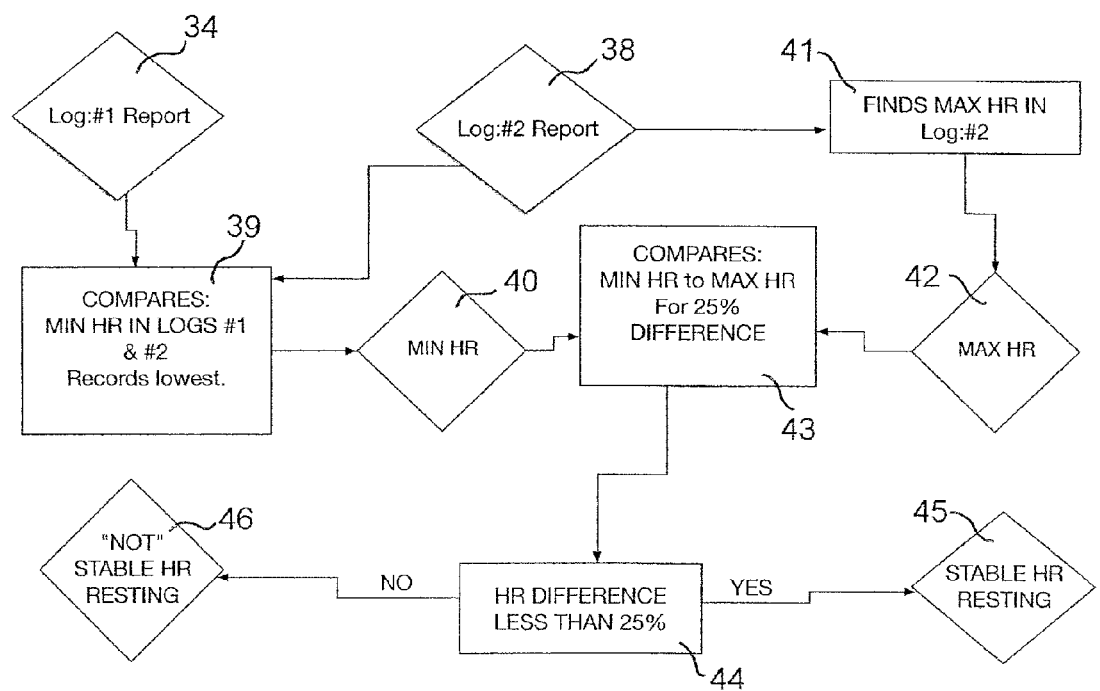
FIG. 4 is the second page of a flowchart of an initial heart screen for the blood pressure device in accordance with the invention.

Referring to FIG. 4, which is a continuation of the flowchart of FIG. 3, the minimum heart rate values from the Log 1 report 34 and the Log 2 report 38 are compared 39 and the lowest value is recorded as the minimum heart rate 40.

Meanwhile, the maximum heart rate value from the Log 2 report 38 is extracted 41 and is recorded as the maximum heart rate 42.

The percentage difference between the minimum heart rate 40 and the maximum heart rate 42 is calculated 43. Where this difference is less than 25% 44, the device 20 concludes that a stable resting heart rate has been reached 45. This stable resting heart rate is referred to as the reference, resting heart rate.

Where the difference is greater than 25% the device 20 concludes that a stable resting heart rate has not been reached 46.

Figure 5:
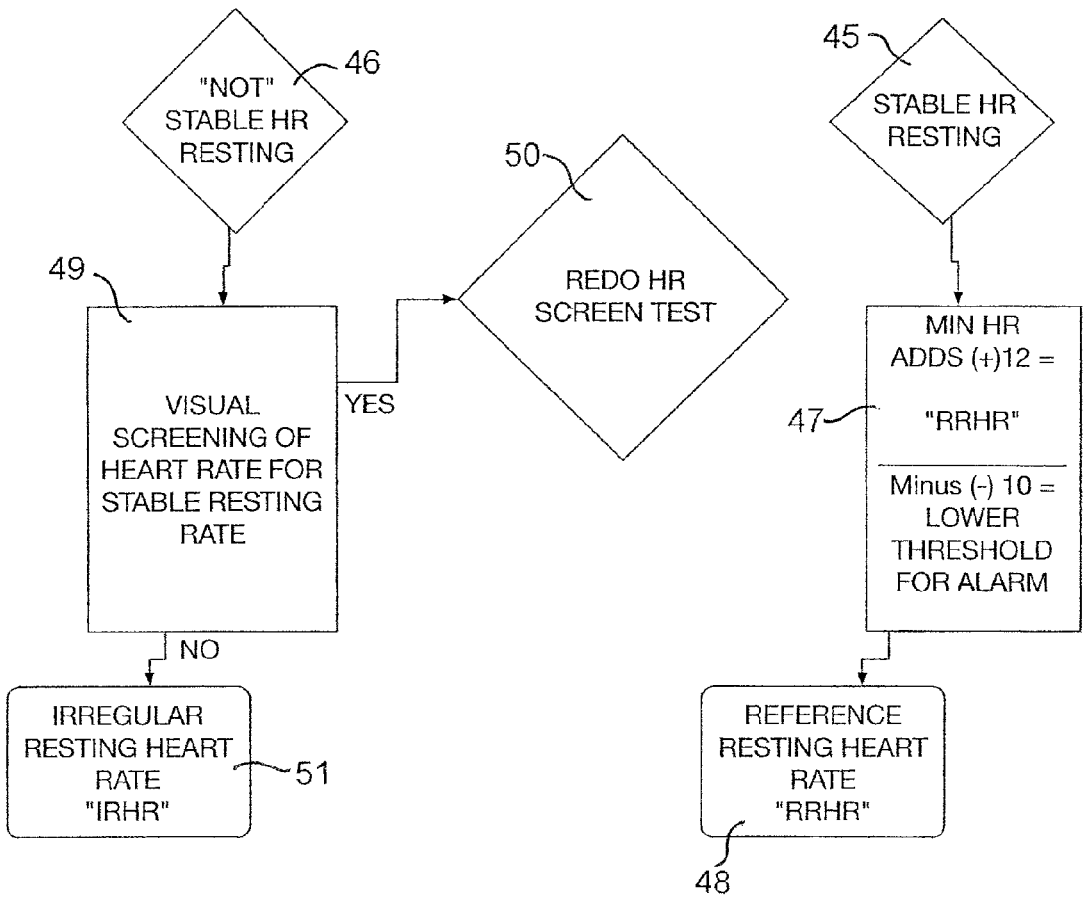
FIG. 5 is the third page of a flow chart of an initial heart screen for the blood pressure device in accordance with the invention.

Referring to FIG. 5, which is a continuation of the flowchart of FIG. 4, where a reference, resting heart rate 45 has been established, a working heart rate window of +12 bpm to −10 bpm of the reference, resting heart rate 45 is calculated 47, and this working heart rate window is used in subsequent blood pressure measurements for the individual 11, as described below. In this instance the screening test is deemed to have been completed and a reference, resting heart rate has been established 48.

The lower limit of −10 bpm for the working heart rate window is included so that if it is exceeded the test will continue to run but a low heart rate alarm will be activated.

Where a stable heart rate has not been found 46, a second by second trace of the heart rate, for the screening test can be referred to 49, and where it is anticipated that a resting heart rate may yet be established, a further screening test may be initiated 50. However, where it cannot be established that a resting heart rate may yet be established, the device 20 records this individual 11 as having an irregular heart rate 51 and the screening test is finished.

Regular Testing.

To perform a routine test using the device 20, the individual 11 adopts a resting position and blood pressure cuff 12 is attached to one upper arm of the individual 11 and the finger clip unit 13 is attached to a finger on the hand of the opposite arm.

The control unit 14 triggers the blood pressure cuff 12 to inflate and deflate three times, with a 180 s interval between each inflation/deflation cycle. This serves to settle the blood pressure cuff 12 on the arm of the individual 11 and relaxes and accustoms the individual 11 to the operation of the device 20. It also serves to check that the blood pressure cuff is operating normally. Once the device 20 has detected that the blood pressure cuff 12 is working normally and is correctly seated on the arm of the individual, a test will commence.

For the individual 11, the initial screening test will have established the presence or absence of a resting heart rate. Thus, where a reference, resting heart rate has been established, this value, together with the working heart rate window, is input into the device 20. The device 20 will then use the reference, resting heart rate protocol to measure the blood pressure.

Where a reference, resting heart rate could not be established following the initial screening test the device 20 will follow the timed protocol to measure the blood pressure.

Figure 6:
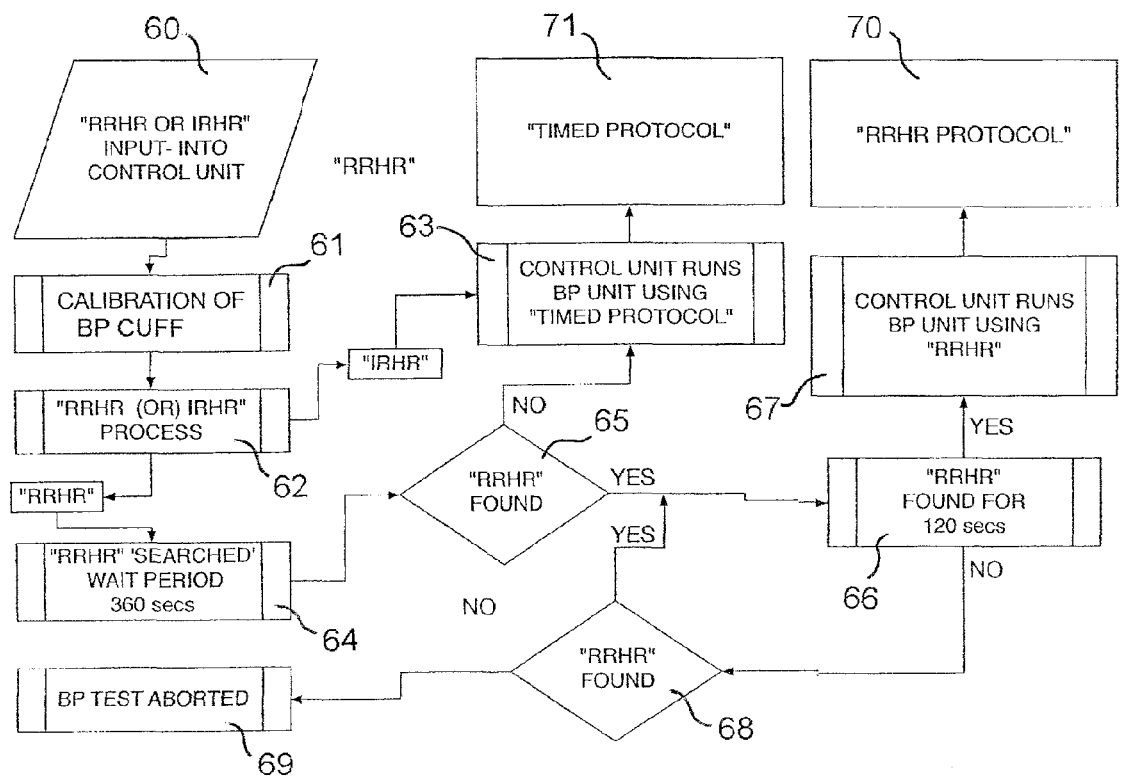
FIG. 6 is a first page of a flowchart comparing the reference, resting heart rate protocol with the timed protocol of the device in accordance with the invention.

Referring to FIG. 6 a flowchart of the steps leading to the running of a test using the reference, resting heart rate protocol or the timed protocol is illustrated.

The parameters for the individual 11 are input into the control unit 14 at the start 60.

The blood pressure cuff 12 is cycled three times, as previously described 61.

The control unit 14 establishes whether it is dealing with a reference, resting heart rate situation or an irregular resting heart rate 62. In the case of an irregular resting heart rate situation, the control unit 14 proceeds immediately to run a test using a timed protocol 63. Otherwise the control unit 14 starts to monitor the heart rate to see if it falls to a value within the working heart rate window 64 the control unit 14 monitors the heart rate at this stage for a total of 360 s.

If after the 360 s interval 64, the heart rate has not fallen to within the working heart rate window, the control unit 14 will decide 65 to continue with the test using the timed protocol 63.

If during the 360 s interval 64 the heart rate remains below the upper limit of the working heart rate window for a period of 120 s, starting within the 360 s interval, the control unit 14 will proceed to run the test using the reference, resting heart rate protocol 67.

Thus, during the 360 s interval the control unit 14 can search for a 120 s interval with the heart rate staying below the upper limit of the working heart rate window a number of times. If the control unit 14 cannot find a 120 s interval the test will be aborted 69. The reference, resting heart rate protocol 70 and the timed protocol 71 are described below with reference to FIG. 7.

Figure 7:
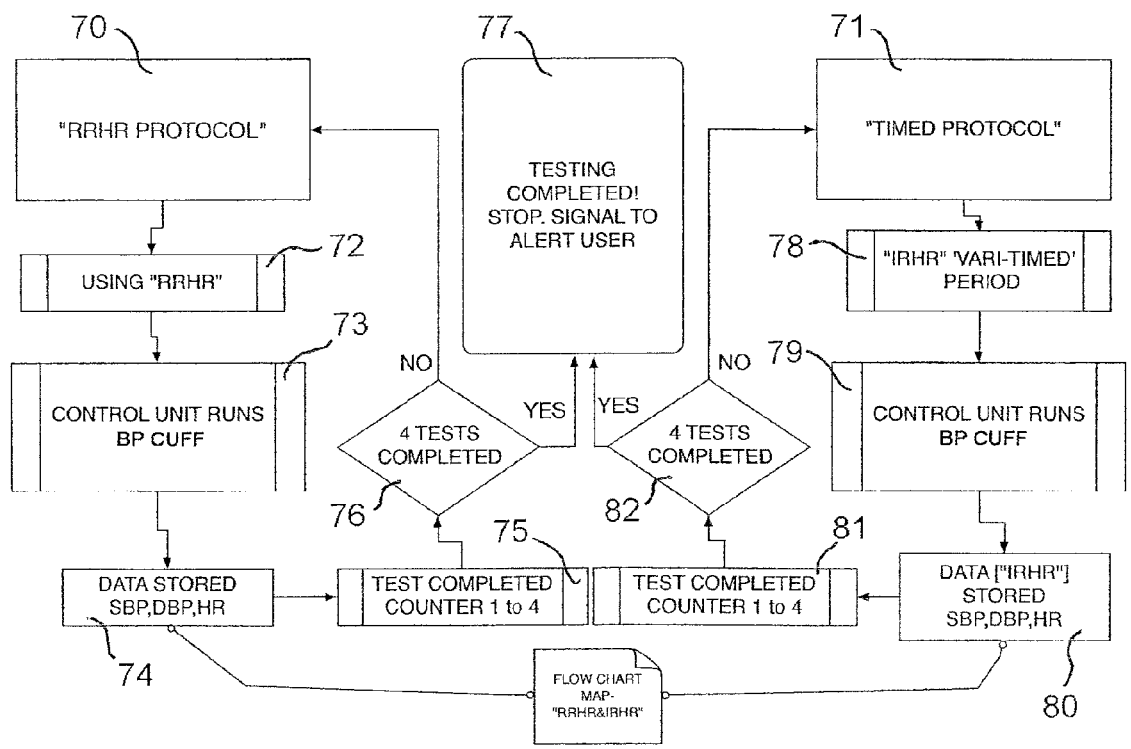
FIG. 7 is a second page of a flowchart comparing the reference, resting heart rate protocol with the timed protocol of the device in accordance with the invention.

Referring to FIG. 7, which illustrates a continuation of the flowchart of FIG. 6, the sequence of steps in a test conducted using the reference, resting heart rate protocol is shown to the left and the sequence of steps in a test conducted using the timed protocol is shown to the right.

Where the heart rate has fallen to below the upper threshold of the working heart rate window and has remained there for a continuous period of 120 s (see above), a test in accordance with the reference, resting heart rate protocol will commence 72. The control unit 14 starts the operation of the blood pressure cuff 12 to measure the blood pressure 73.

At the completion of each successful blood pressure reading the SBP, DBP and HR values are stored 74 and a counter is incremented 75. If four sets of data have been stored, i.e. four completed tests 76, the control unit 14 stops the blood pressure cuff 12 and gives an indication that the test is complete 77. Otherwise, the control unit 14 will start the blood pressure cuff 12 again 70 to obtain a further set of data.

Alternatively, where an irregular heart rate has been found a test in accordance with the timed protocol will commence 78. The control unit 14 starts the operation of the blood pressure cuff 12 to measure the blood pressure 79.

At the completion of each successful blood pressure reading the SBP, DBP and HR values are stored 80 and a counter is incremented 81. If four sets of data have been stored, i.e. four completed tests 82, the control unit 14 stops the blood pressure cuff 12 and gives an indication that the test is complete 77. Otherwise, the control unit 14 will start the blood pressure cuff 12 again 71 to obtain a further set of data.

Figure 8:
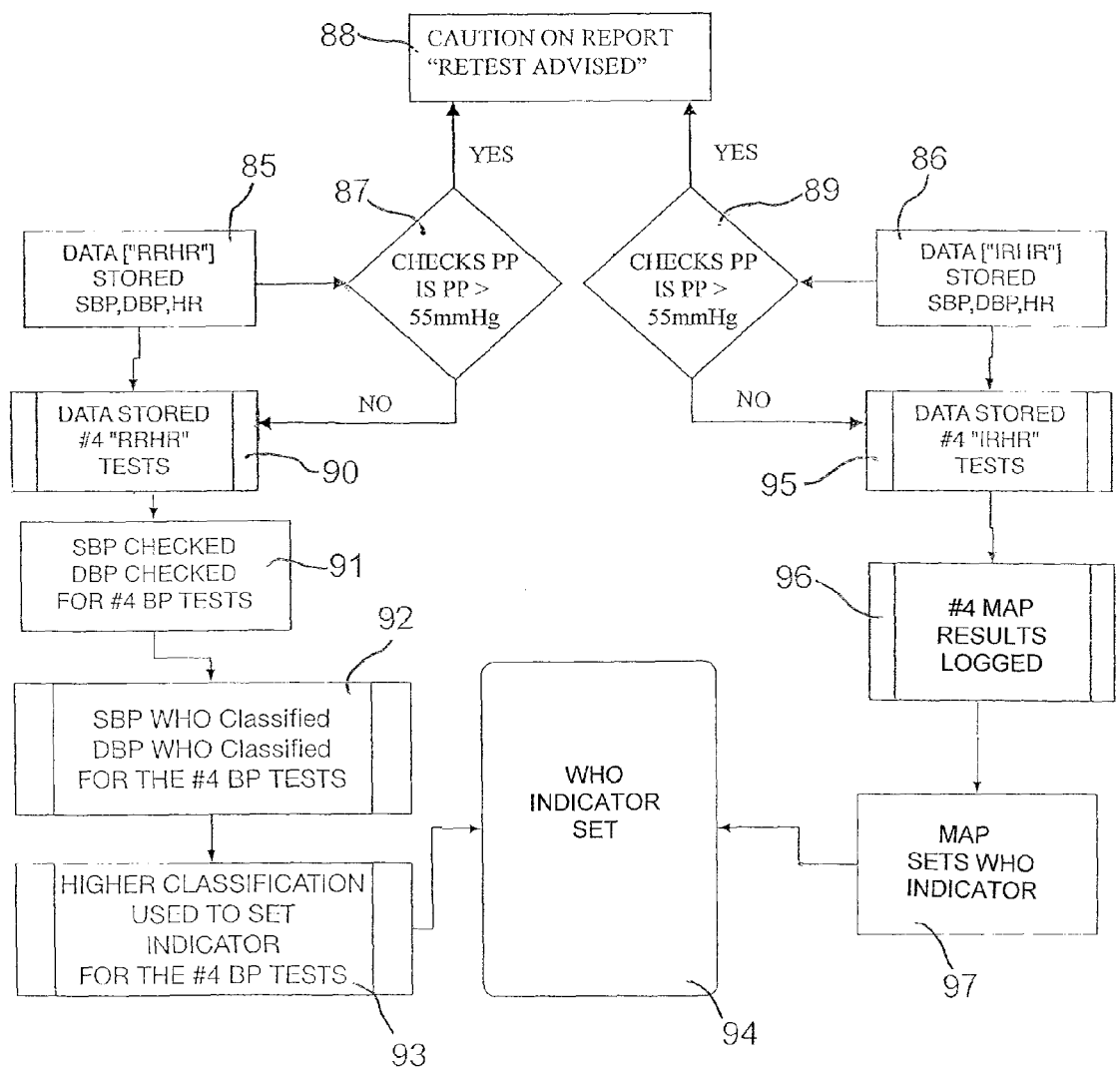
FIG. 8 is a third page of a flowchart comparing the reference, resting heart rate protocol with the timed rate protocol of the device in accordance with the invention.

Referring to FIG. 8, which illustrates a continuation of the flowchart of FIG. 7, the processing of the sets of data, obtained using the reference, resting heart rate protocol 85, is shown to the left and the processing of the sets of data, obtained using the timed protocol 86, is shown to the right.

The PPs for the data at 85 are calculated and if a PP>55 mmHg is found 87 the report will be flagged "RETEST ADVISED" 88.

Similarly the PPs for the data at 86 are calculated and if a PP>55 mmHg is found 89 the report will be flagged "RETEST ADVISED" 88, except in the case where arrhythmia has been found.

Where an individual cannot reach a fully rested state before the blood pressure measurement is initiated, nevertheless the device will run the tests in accordance with the appropriate protocol, so that a blood pressure reading is available for monitoring purposes. The resulting report will be flagged "RETEST ADVISED" to indicate that the PP has not dropped below 60 mgHg, which infers that the brachial artery has not dilated.

Continuing with the RRHR protocol side of the flowchart,

The SBP and DBP are checked for the four sets of tests 91 and the SBP and DBP are classified in accordance with the WHO classification for the four sets of tests 92. The higher WHO classification, assigned at 92 is used for setting a WHO Indicator 93, which when set 94, completes the test and a report can now be compiled.

Alternatively, in the case of tests being run in accordance with the timed protocol 86 the data is stored as four tests 95. The MAP is calculated for each set of data 96. The MAP value is used for setting a WHO Indicator 97, which when set 94, completes the test and a report can now be compiled.

The final report will include the WHO Indicator which is a coloured bar, with an indicator line thereon, showing into which WHO blood pressure classification the individual's MAP falls.

Figure 9:
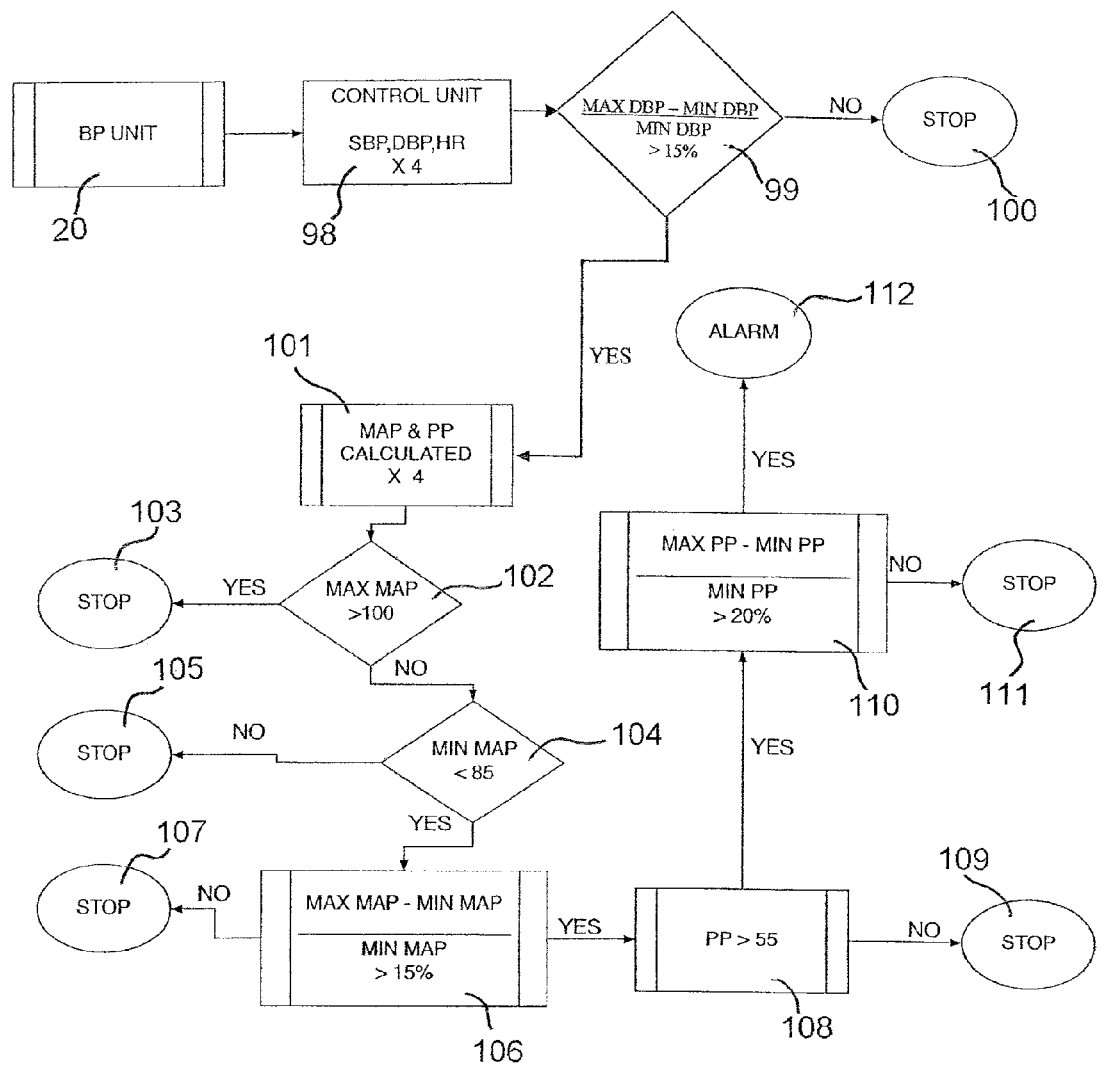
FIG. 9 is a flowchart of an aortic regurgitation screening protocol in accordance with the invention.

Referring to FIG. 9, a flowchart of an aortic regurgitation screening protocol in accordance with the invention is shown. This screening test is carried out on individuals between the ages of 15 and 40 years.

The blood pressure device 20 is used to obtain four sets of data 98. If the percentage difference between the maximum DBP and the minimum DBP is greater than 15% 99 then the MAP and PP are calculated for each set 101, otherwise the protocol is aborted 100.

At the data centre 22 (FIG. 2) the highest MAP value is checked 102. If it is greater than 100 mmHG the screening test is aborted 103. However, if no one of the MAP values is greater than 100 mmHG the lowest MAP value is checked to see if it is less than 85 mmHg 104. If this is not the case then the screening test is aborted 105.

If the minimum MAP value is less than 85 mmHg then the data centre 22 calculates the proportional difference between the highest and lowest MAP values 106 in accordance with the formula $$\frac{(\text{MAX MAP} - \text{MIN MAP})100\%}{\text{MIN MAP}}$$

If the proportional difference is less than 15% the screen test is aborted 107. However, if the proportional difference is greater than 15% the pulse pressure value is checked 108.

If the highest pulse pressure value 108 is less than 55 mmHG then the screen test is aborted 109.

If the highest pulse pressure value 108 is greater than 55 mmHg then the data centre compares the highest and lowest pulse pressure readings 110 in accordance with the following formula $$\frac{(\text{MAX } PP - \text{MIN } PP)100\%}{\text{MIN } PP}$$

If this value is less than 20% the screen test is aborted 111. However, if this value is greater than 20% the screening test is complete and the results will indicate that the individual may have aortic regurgitation, the report will reflect this, and further investigations will be recommended. The data centre 22 will alert the monitoring centre 23, which will issue an alarm for this individual 112.

Alarm Events

Alarm events occur when an individual's 11 blood pressure test results, or the individual's 11 inability to perform a test, indicate that intervention and reassessment is required. The specific thresholds for alarm events can vary from individual to individual depending upon their circumstances. Examples of alarm events include:

Individual's MAP passes the 101 mmHg threshold
    If the individual's 11 MAP rises above 101 mmHg, he is moving towards $1^{st}$ stage hypertension. This is treated as an alarm event and intervention is needed to reverse the increasing blood pressure and bring it within the normal range.

The individual 11 becomes hypertensive

MAP is lowering/rising too quickly

A rise/fall of more than 15 mmHg from the individual's 11 initial MAP measurement is an alarm event that requires reassessment of the individual's 11 profile. The reference MAP may be reset and a tighter volatility tolerance applied, depending on the MAP measurement.

Excessively high/low MAP measurement

If the individual's 11 MAP drops below 86 mmHg

If the individual's 11 MAP rises above a specified level.

Resting heart rate is persistently above reference, resting heart rate range.

Resting heart rate is over 5 bpm below the reference, resting heart rate

Resting heart rate is over 10 bpm below the reference, resting heart rate

The invention claimed is:

1. A device for measuring brachial arterial blood pressure, comprising:
a cuff including a brachial pressure sensor for generating a brachial pressure signal corresponding to a brachial pressure of a first brachial artery;
a heart rate sensor for generating a heart rate signal of a heart rate at a vessel not downstream of the first brachial artery so that a heart rate measured by the heart rate sensor is not impacted by a pressure applied by the cuff; and
a control unit connected to both the brachial pressure sensor and the heart rate sensor for collecting signals therefrom, the control unit including:
a storage medium for storing a reference, resting heart rate of a user; and
a processor configured to determine a stable parasympathetic state of the brachial artery by comparing signals from the heart rate sensor and comparing the signals against the reference resting heart rate, which reference, resting heart rate has been previously established for the user during initial assessment by monitoring a heart rate for a period of 1000 to 1400 s and identifying a minimum heart rate for the period, which minimum heart rate is defined as the reference, resting heart rate for the user;
the processor further configured to initiate a blood pressure evaluation using a resting heart rate protocol, once the measured heart rate has dropped to within +12 bpm of the reference, resting heart rate for the user;
the processor further configured to initiate a blood pressure evaluation using a timed protocol, where the measured heart rate does not remain at or below +12 bpm of the reference, resting heart rate for a period within the range of 100 to 140 s, due to the presence of arrhythmia;
the processor further configured to receive signals from the brachial pressure sensor and establish a mean arterial pressure (MAP), a pulse pressure (PP), and any arrhythmia from the signals, and write to a storage the pulse pressure, mean arterial pressure, and blood pressure readings in a stored data set; and
the processor further configured to send an alert if the pulse pressure is greater than 55 mmHg unless an arrhythmia is determined by the processor from the heart rate signals.

2. The device according to claim 1, wherein the heart rate sensor is a finger clip heart rate monitor.

3. The device according to claim 1, wherein four sets of data are written to the storage.

4. The device according to claim 3, wherein the control unit analyses the four sets of data and classifies the blood pressure into one of six WHO (World Health Organization) classifications using the systolic or diastolic pressure value, whichever value results in the higher classification.

5. A system for measuring brachial arterial blood pressure, comprising:
a cuff including a brachial pressure sensor for generating a brachial pressure signal corresponding to a brachial pressure of a first brachial artery;
a heart rate sensor for generating a heart rate signal of a heart rate at a vessel not downstream of the first brachial artery so that a heart rate measured by the heart rate sensor is not impacted by a pressure applied by the cuff;
a control unit connected to both the brachial pressure sensor and the heart rate sensor for collecting signals therefrom, the control unit including:
a storage medium for storing a reference resting heart rate of a user; and
a processor configured to determine a stable parasympathetic state of the brachial artery by comparing signals from the heart rate sensor and comparing the signals against the reference, resting heart rate, which reference, resting heart rate has been previously established for the user during initial assessment by monitoring a heart rate for a period of 1000 to 1400 s and identifying a minimum heart rate for the period, which minimum heart rate is defined as the reference, resting heart rate for the user;
the processor further configured to initiate a blood pressure evaluation using a resting heart rate protocol, once the measured heart rate has dropped to within +12 bpm of the reference, resting heart rate for the user;
the processor further configured to initiate a blood pressure evaluation using a timed protocol, where the measured heart rate does not remain at or below +12 bpm of the reference, resting heart rate for a period within the range of 100 to 140 s, due to the presence of arrhythmia;
the processor further configured to receive signals from the brachial pressure sensor and establish a mean arterial pressure (MAP), a pulse pressure (PP), and any arrhythmia from the signals, and write to a storage the pulse pressure, mean arterial pressure, and blood pressure readings in a stored data set;
the processor further configured to send an alert if the pulse pressure is greater than 55 mmHg unless an arrhythmia is determined by the processor from the heart rate signals; and
the control unit having means for transmitting the and each set of data to the remote data centre.

6. The system according to claim 5, wherein four sets of data are written to the storage.

7. The system according to claim 6, wherein, where the individual's age is within the range of 10 to 50 years and one of the recorded MAP readings is less than 100+/−5 mmHg, the control unit compares the percentage difference of the four MAPs recorded and where the percentage difference is greater than 13 to 17% then, where one of the PP readings is greater than 55+/−5 mmHg, the control unit compares the percentage difference of the four recorded PPs, and where the percentage difference is greater than 18 to 22%, the report will include an indication of a possible presence of aortic valve regurgitation.

8. The system according to claim 6, wherein, where the individual's age is within the range of 15 to 40 years and one of the recorded MAP readings is less than 100 mmHg, the control unit compares the percentage difference of the four MAPs recorded and where the percentage difference is greater than 15% then, where one of the pulse pressure readings is greater than 55 mmHg, the control unit compares the percentage difference of the four recorded PPs, and where the percentage difference is greater than 20%, the report will include an indication of the possible presence of aortic valve regurgitation.

9. The system according to claim 7 or 8, wherein a drop in the diastolic blood pressure of between 8 to 15% from the value recorded during a previous testing session triggers the device to check for the possible presence of aortic valve regurgitation.

10. The system according to claim 7 or 8, wherein the control unit checks the PP readings before, if necessary, checking the MAP readings.

\* \* \* \* \*